(12) United States Patent
Sturgeon et al.

(10) Patent No.: US 12,076,005 B2
(45) Date of Patent: Sep. 3, 2024

(54) VIDEO-BASED ANALYSIS OF STAPLING EVENTS DURING A SURGICAL PROCEDURE USING MACHINE LEARNING

(71) Applicant: Verb Surgical Inc., Santa Clara, CA (US)

(72) Inventors: Darrick Tyler Sturgeon, Oakland, CA (US); Jocelyn Elaine Barker, San Jose, CA (US); Varun Kejriwal Goel, Oakland, CA (US); Taylor W. Aronhalt, Loveland, OH (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/188,163

(22) Filed: Mar. 22, 2023

(65) Prior Publication Data

US 2023/0301648 A1    Sep. 28, 2023

Related U.S. Application Data

(60) Provisional application No. 63/323,046, filed on Mar. 23, 2022.

(51) Int. Cl.
*A61B 17/068* (2006.01)
*A61B 17/072* (2006.01)
(Continued)

(52) U.S. Cl.
CPC .......... *A61B 17/068* (2013.01); *A61B 17/072* (2013.01); *A61B 17/115* (2013.01);
(Continued)

(58) Field of Classification Search
CPC ................ A61B 17/068; A61B 17/072; A61B 17/07207; A61B 17/115; A61B 34/20;
(Continued)

(56) References Cited

U.S. PATENT DOCUMENTS 4,907,973 A * 3/1990 Hon ...................... G09B 23/285
434/262
5,791,907 A * 8/1998 Ramshaw ............ G09B 23/285
434/323
(Continued)

FOREIGN PATENT DOCUMENTS

CN    112750344    5/2021
KR    102180921    11/2020
WO    2021252384   12/2021

OTHER PUBLICATIONS

International Search Report and Written Opinion in PCT/IB2023/052826 dated Jul. 7, 2023 (8 pages).

*Primary Examiner* — Scott A Smith
(74) *Attorney, Agent, or Firm* — AMSEL IP LAW PLLC; Jason Amsel

(57) ABSTRACT

An analysis system trains a machine learning model to detect stapling events from a video of a surgical procedure. The machine learning model detects times when stapling events occur as well as one or more characteristics of each stapling event such as length of staples, clamping time, or other characteristics. The machine learning model is trained on videos of surgical procedures identifying when stapling events occurred through a learning process. The machine learning model may be applied to an input video to detect a sequence of stapler events. Stapler event sequences may furthermore be analyzed and/or aggregated to generate various analytical data relating to the surgical procedures for applications such as inventor management, performance evaluation, or predicting patient outcomes.

20 Claims, 4 Drawing Sheets

(51) Int. Cl.
*A61B 17/115* (2006.01)
*G06V 10/774* (2022.01)
*A61B 1/00* (2006.01)
*A61B 17/00* (2006.01)
*A61B 34/00* (2016.01)
*A61B 34/20* (2016.01)
*A61H 31/00* (2006.01)
*G06F 3/0482* (2013.01)
*G06V 10/764* (2022.01)
*G06V 10/778* (2022.01)

(52) U.S. Cl.
CPC ........ *G06V 10/774* (2022.01); *A61B 1/00193* (2013.01); *A61B 2017/00367* (2013.01); *A61B 34/20* (2016.02); *A61B 34/71* (2016.02); *A61H 31/00* (2013.01); *G06F 3/0482* (2013.01); *G06V 10/764* (2022.01); *G06V 10/7788* (2022.01)

(58) Field of Classification Search
CPC ......... A61B 34/30; A61B 34/37; A61B 34/71; A61B 34/76; A61B 1/00193; A61B 1/00194; A61B 1/3132; A61B 90/36; A61B 90/37; A61B 2017/00367; A61B 2017/07214; G06V 10/761; G06V 10/764; G06V 10/774; G06V 10/7788; G06V 10/7715; G06V 10/945; G06V 20/70; A61H 31/00; A61H 31/006; A61H 31/007; G06F 3/0482; G06F 3/0488; G06F 18/41; G06F 18/2178; G09B 5/065; G09B 5/02; G09B 23/28
USPC ..... 227/19, 175.1, 175.2, 176.1; 606/1, 139, 606/219; 382/103, 159, 181, 278; 434/156, 236, 238, 262, 266, 350; 600/407, 408, 425
See application file for complete search history.

(56) References Cited

U.S. PATENT DOCUMENTS

| | | | | |
|---|---|---|---|---|
| 5,853,292 | A * | 12/1998 | Eggert | G09B 23/28 434/266 |
| 6,386,882 | B1 * | 5/2002 | Linberg | G16H 40/63 434/262 |
| 6,535,714 | B2 * | 3/2003 | Melker | G09B 7/02 434/350 |
| 7,056,123 | B2 * | 6/2006 | Gregorio | A61B 34/71 434/262 |
| 7,594,815 | B2 * | 9/2009 | Toly | G09B 23/285 434/262 |
| 8,469,713 | B2 * | 6/2013 | Kron | G09B 5/065 434/156 |
| 10,182,966 | B2 * | 1/2019 | Freeman | A61H 31/00 |
| 10,912,619 | B2 * | 2/2021 | Jarc | G09B 23/285 |
| 11,058,501 | B2 * | 7/2021 | Tokarchuk | G16H 40/67 |
| 2009/0088634 | A1 * | 4/2009 | Zhao | A61B 1/00193 600/425 |
| 2011/0301447 | A1 * | 12/2011 | Park | G06T 7/0016 600/407 |
| 2015/0086133 | A1 * | 3/2015 | Grady | G06F 16/5866 382/278 |
| 2015/0106117 | A1 * | 4/2015 | Ananda | G16H 50/20 705/3 |
| 2015/0297313 | A1 * | 10/2015 | Reiter | A61B 5/7267 600/408 |
| 2016/0171682 | A1 * | 6/2016 | Abedini | G16H 30/20 382/132 |
| 2019/0201102 | A1 | 7/2019 | Shelton, IV et al. | |
| 2019/0201124 | A1 | 7/2019 | Shelton, IV et al. | |
| 2019/0201126 | A1 | 7/2019 | Shelton, IV et al. | |
| 2020/0082934 | A1 | 3/2020 | Venkataraman | |
| 2020/0258616 | A1 | 8/2020 | Likosky | |
| 2021/0290317 | A1 * | 9/2021 | Sen | G06N 3/047 |
| 2023/0177703 | A1 * | 6/2023 | Fathollahi | G06V 10/7715 382/103 |
| 2023/0301648 | A1 * | 9/2023 | Sturgeon | A61B 17/068 |

* cited by examiner

VIDEO-BASED ANALYSIS OF STAPLING EVENTS DURING A SURGICAL PROCEDURE USING MACHINE LEARNING

CROSS-REFERENCE TO RELATED APPLICATIONS

This application claims priority to U.S. Provisional Application No. 63/323,046, filed Mar. 23, 2022, which is incorporated by reference in its entirety.

BACKGROUND

Technical Field

The described embodiments relate to a machine learning technique for detecting and analyzing surgical stapling events from video of a surgical procedure.

Description of the Related Art

Many surgical procedures (e.g., sleeve gastrectomy, Roux-en-Y gastric bypass, etc.) involve surgical stapling. Surgeons have a variety of choices when performing surgical stapling. For example, surgical staples are available in different lengths, different manufacturers, and are available with or without buttresses. For surgical procedures involving multiple surgical staples, a surgeon must decide which type of staple to use for different purposes as well as the specific sequence to deploy the staples during the procedure. Different choices relating to surgical stapler usage can have significantly impact on inventory costs, surgery times, and patient outcomes.

BRIEF DESCRIPTION OF THE DRAWINGS

Figure (FIG. 1 is an example embodiment of a system for detecting and characterizing stapling events from video of a surgical procedure.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made to several embodiments, examples of which are illustrated in the accompanying figures. Wherever practicable, similar or like reference numbers may be used in the figures and may An analysis system trains a machine learning model to detect stapling events from a video of a surgical procedure. The machine learning model detects times when stapling events occur as well as one or more characteristics of each stapling event such as length of staples, clamping time, or other characteristics. The machine learning model is trained on videos of surgical procedures identifying when stapling events occurred through a learning process. The machine learning model may be applied to an input video to detect a sequence of stapler events. Stapler event sequences may furthermore be analyzed and/or aggregated to generate various analytical data relating to the surgical procedures for applications such as inventory management, performance evaluation, or predicting patient outcomes.

Figure 1:
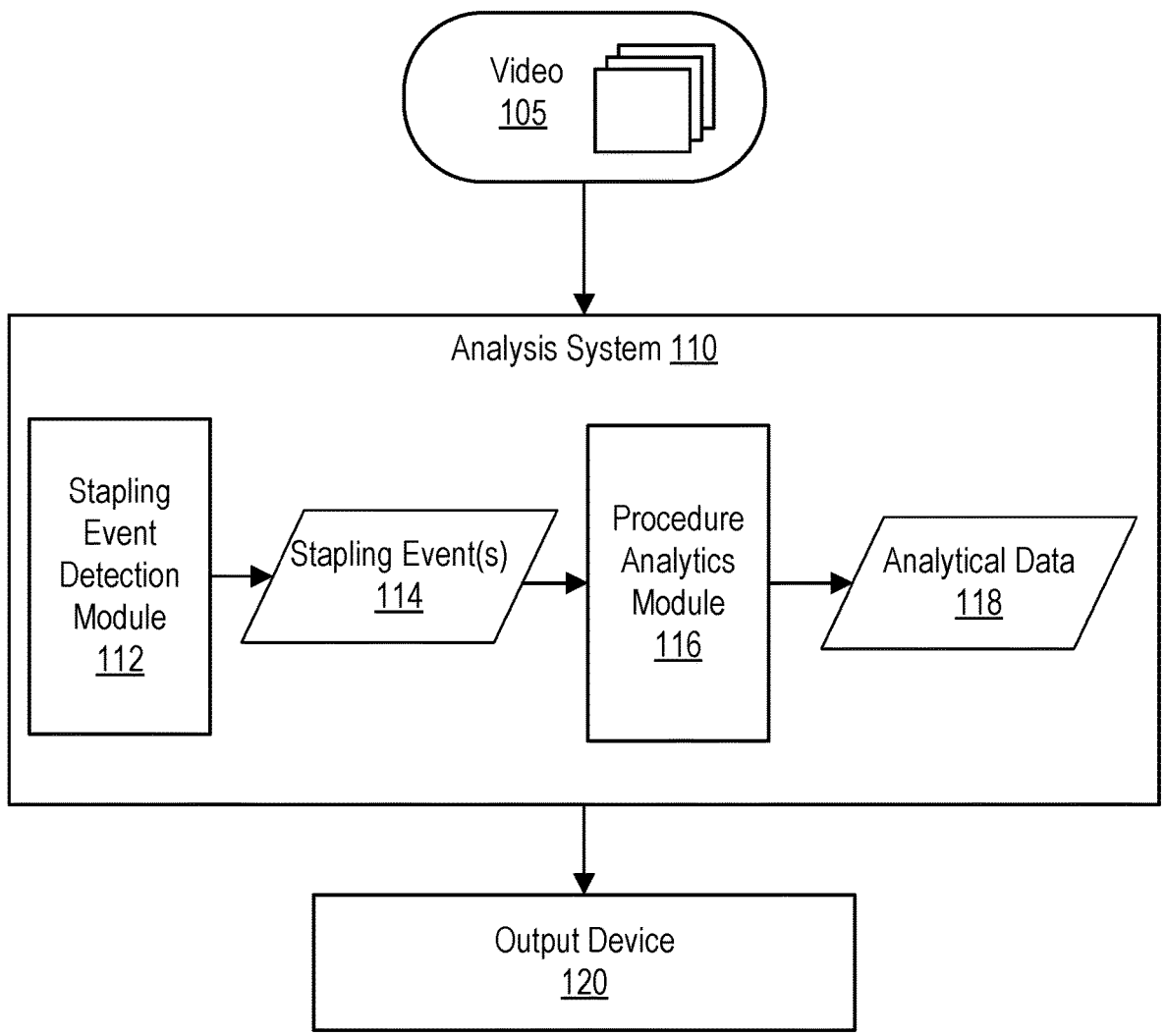

FIG. 1 illustrates an example embodiment of a system 100 for detecting and for characterizing stapling events from video 105 of one or more surgical procedures. Each stapling event involves delivery of one or more staple loads to tissue of a patient during a medical procedure using a stapler device. The stapler loads are typically arranged in a cartridge of multiple staples of the same type which are delivered concurrently by the stapler upon actuation. The type of stapler load may be characterized by its manufacturer, length, color, presence or absence of buttress, type of buttress, or other differentiating characteristics. The color of a stapler load is generally related to the length of the staplers by a predefined color coding. The specific color coding may vary for different stapler manufacturers. A stapling event may also include various pre-actuation or post-actuation activities relating to the stapling event. For example, a surgeon may often perform a clamping of the tissue prior to actuating the stapler. Various medical procedures may involve different sequences of stapling events that may occur with various timing and may involve individual stapling events utilizing different types of stapler loads, different counts of stapler loads, and different event durations.

The video 105 of the surgical procedure may be captured by one more cameras positioned to have a field of view of the anatomy where the stapling events are performed. For example, the video 105 may be obtained from an overhead camera in the operating room, a head mounted camera worn by a surgeon, an endoscopic camera, or a combination thereof. In an embodiment, the video 105 may include (or be associated with) various metadata related to the surgical procedure depicted in the video 105. For example, the metadata may identify the type of procedure being performed, information about the patient undergoing the procedure, the surgeon (or other medical practitioner), that facility where the surgery takes place, and outcome information associated with the surgery such as patient recovery time, onset of complications, or other metrics characterizing the outcome.

The analysis system 110 includes a stapling event detection module 112 and a procedure analytics module 126. The stapling event detection module 112 may automatically detect the stapling events 114 in a received video 105. Each detected stapling event 114 may be characterized according to timing data indicating when the stapling event 114 occurred and one or more characteristics of each stapling event 114. The timing data may comprise a single timestamp (e.g., defining a video frame) or a time interval (e.g., defining a video segment). The timing data may be specified relative to a start of the video or with respect to frame numbers, or may be specified relative to a detected start of the surgical procedure. The characteristics of each stapling event 114 detectable by the stapling event detection module 112 may include, for example, an identification of a stapler manufacturer, a color of the stapler load and/or the corresponding length of the staples (based on the relevant color coding for the identified manufacturer), presence or absence of a buttress in the staple load, type of buttress, a number of times a stapler was fired during the stapling event, a count of staplers deployed, a duration of the stapling event, a clamping time during which tissue was clamped in association with the stapling event 114, and/or other characteristics.

The stapling events 114 may be organizing as a stapling event sequence associated with the surgical procedure depicted in the video 105. Here, a stapling event sequence may involve multiple stapling events that may each utilize the same or different types of staple loads and/or may have other differing characteristics. In an embodiment, the stapling event detection module 112 may detect the stapling events 114 in substantially real-time based on a live input video 105.

The procedure analytics module 116 generates various analytical data 118 associated with the detected stapling events 114 that may be utilized for applications such as inventory management, performance evaluation, and/or patient outcome predictions. The analytical data 118 may be based on a single sequence of stapling events 114 associated with a single input video 105 for a single medical procedure, or may be based on aggregated sequences of stapling events 114 across multiple videos 105 of medical procedures of the same or different type. For example, the procedure analytics module 116 may aggregate sequences of stapler events 114 to detect aggregate information relating to inventory management such as counts of different types of stapler loads used, rates of usage, etc. Furthermore, the procedure analytics module 116 may aggregate stapling events 114 based on various filtering parameters such as type of procedure, medical practitioners involved, location of the procedure, etc. For example, the procedure analytics module 116 may determine the average stapler lengths used for a particular medical procedure, average number of stapling events per medical procedure, or other aggregate data that may be indicative of most common practices. In another example, the procedure analytics module 116 may generate aggregate analytic data 118 characterizing sequences of stapling events 114 across multiple different types of surgical procedures. In another example, the procedure analytics module 116 may generate analytical data 118 indicating how commonly one staple load color (or length) follows another stapler load color (or length) over a range of different procedures.

The procedure analytics module 116 may furthermore generate various analytical data indicative of comparisons between different sequences of stapling events 114. For example, the procedure analytics module 116 may generate an out that compares a detected sequence of stapling events 114 for a specific observed medical procedure to a baseline sequence of stapling events associated with the medical procedure and derive a similarity metric. The baseline sequence may be derived from observed sequences for similar procedures or may be input from an expert knowledge source. The similarity metric may be indicative of how closely the observed sequence conforms to the baseline in terms of types of staplers used, timing of the stapling events, clamping time, or other characteristics. This information may furthermore be used to automatically detect anomalies in a specific observed procedure that deviate significantly from common practice. This type of information may be utilized to characterize performance of a medical practitioner and/or predict patient outcomes.

In further embodiments, the procedure analytics module 116 may generate various outcome predictions based on the observed sequence of stapling events 114. For example, the analysis system 110 may aggregate observed stapling events 114 and correlate the sequences to observed patient outcomes. These correlations may be used to predict an outcome associated with a specific observes sequence of stapling events 114. For example, the procedure analytics module 116 may predict an expected patient recovery times and/or likelihoods of complications based at least in part on the detected sequence of stapling events 114.

The procedure analytics module 116 may generate various visualizations or other outputs (e.g., audio outputs) relating to the detected stapling events 114 and/or the analytical data 118. For example, for a specific video 105, the procedure analytics module 116 may generate a timeline that indicates relative timing of each stapling event 114 during the medical procedure and one or more characteristics of each stapling event (such as the load color). The procedure analytics module 116 may furthermore automatically generate alerts indicative of detected deviations from standard practice and/or detected outcome predictions.

In an embodiment, the procedure analytics module 116 may detect at least some analytical data 118 relating to an input video 105 in substantially real-time such that analytical data 118 can be output during the medical procedure. In this case, the procedure analytics module 116 may generate specific recommendations to guide a medical practitioner through a surgery. For example, for a known medical procedure comprising a sequence of surgical steps, the procedure analytics module 116 may detect which steps have been performed based on the detected stapling events 114 and generate outputs indicative of the recommended next steps. Furthermore, the procedure analytics module 116 may generate specific recommendation regarding the type (e.g., color) of stapler loads to be applied during the medical procedure based on an observed sequence of stapling events 114 and other metadata associated with the medical procedure.

The output device 120 may receive the stapling event 114, the analytical data 118, the input video 105, and/or other metadata from the analysis system 110 and generate one or more outputs from presentation. The output device 120 may comprise a computing system (e.g., a mobile device, tablet, laptop, or desktop computer) that may present user interface for presenting the stapling events 114 and/or the analytical data 118. The sequence of stapling events 114 may be represented in a graphical interface indicating respective timing data associated with each stapling event 114 and respective characteristics of the events 114. In some embodiments, the timing data may be presented together with the video 105 (e.g., as a visual overlay) and/or associated metadata (e.g., identifying the procedure, patient, surgeon, facility, etc.) The user interface can further enable access to various aggregated analytical data 118 described above in the form of charts, graphs, tables, or other data presentation structures. In further embodiments, the output device 120 could include an audio output device that generates audio data indicative of the stapling events 114 and/or the analytical data 118. For example, in a real-time analysis, the output device 120 may output recommended steps for the surgical procedure as audio outputs.

The output device 120 may furthermore comprise an indexed database of stapling events 114 and/or analytical data 118 that can be accessed according to various search queries or filters. For example, such a database may be utilized to view historical stapling sequences associated with a particular type of surgery, stapling sequences utilized by a particular physician, relative counts of different types of stapling used per medical facility, or other information.

The above-described analysis system 110 may be employed for various purposes in association with a healthcare provider. For example, in one application, the detected stapling events may be processed through an inventory management system to track inventory of staple loads and facilitate reordering. Here, the inventory management system may automatically reorder staples when tracked inventory drops below a threshold level and/or may alert an administrator. In another example application, the analysis system 110 may be utilized to evaluate performance of a surgeon based on factors such as conformance to baseline standards associated with stapling sequences, number of staple loads used per medical procedure, durations of stapling sequences or other performance metrics. In further example applications, the analysis system 110 may learn best practices by correlating different stapler sequences with respective outcomes to identify potential cause and effect relationships.

Figure 2:
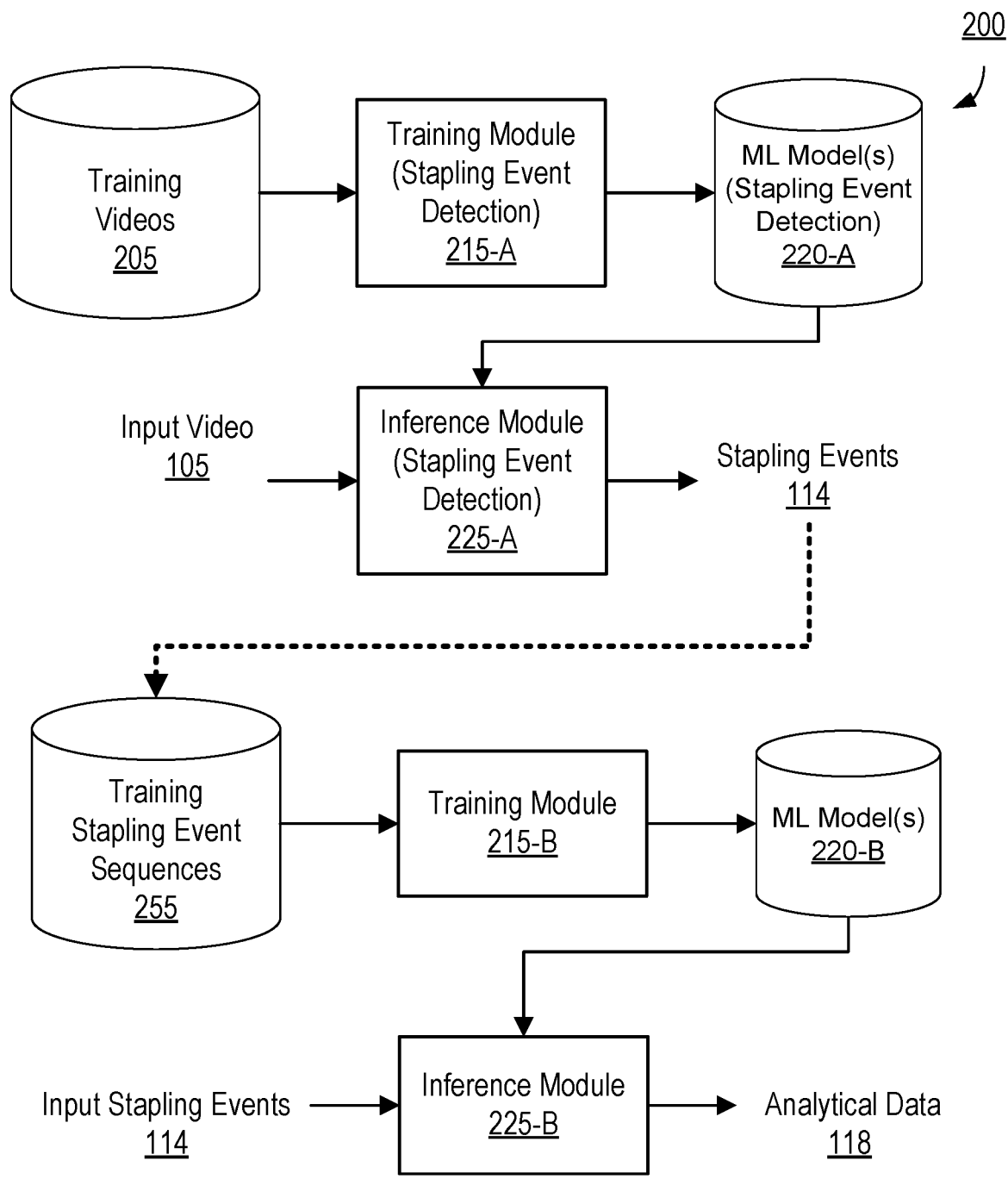
FIG. 2 is an example embodiment of a machine learning system for detecting one or more stapling events and characteristics of stapling events from video of a surgical procedure.

FIG. 2 illustrates an example embodiment of machine learning system 200 that can be used to implement various aspects of the analysis system 110 described above. The machine learning system 200 includes a training video store 205, a training stapling event sequences store 255, training modules 215-A, 215-B for stapling event detection and analytical predictions respectively (collectively referred to herein as training modules 215), machine learning model stores 220-A, 220-B for stapling event detection and analytical predictions respectively (collectively referred to herein as machine learning model stores 220), and inference modules 225-A, 225-B for stapling event detection and analytical predictions respectively (collectively referred to herein as inference modules 225). In other embodiments the machine learning system 200 may comprise different or additional components than those described in conjunction with FIG. 2.

The training video store 205 stores training videos for training one or more machine learning models 220-A associated with stapling event detection. The training videos 205 each depict medical procedures and are associated with labels characterizing stapling events in the procedures. Different labels may be associated on a per-frame basis, on a per-segment basis, and/or on a full video basis. For example, labels may indicate timing of stapling events (e.g., whether or not a stapling event is occurring on a per-frame or per-segment basis) and one or more characteristics of each stapling event. A stapling event may include a single deployment of a staple load or may include a sequence of deployments. Labeled characteristics of a stapling event may include, for example, a color and/or associated length of a load of staples used in a stapling event, presence or absence of a buttress in a staple load applied during the stapling event, type of buttress, a manufacturer of a stapler used during the stapling event, a count of staplers deployed, a duration of the stapling event, a length of time the stapler clamped together tissue of a patient (i.e., a clamping time), a firing rate of the stapler, and other characteristics describing usage of staples during the stapling event. In various embodiments, labels are obtained for the training videos 205 from expert reviewers tasked with annotating the video.

The training data may furthermore include various metadata associated with surgical procedures depicted in the videos. For example, the training data may include information about the patient undergoing the procedure, the surgeon (or other medical practitioner), that facility where the surgery takes place, and outcome information associated with the surgery such as patient recovery time, onset of complications, or other metrics characterizing the outcome.

The training module 215-A trains one or more machine-learning models 220-A for stapling event detection. In various embodiments, the training module 215-A may generate the machine learning model 220-A based on learning techniques such as regression, support vector machines, naïve bayes, decision trees, k nearest neighbors, random forest, boosting algorithms, k-means, hierarchical clustering, neural networks, multilayer perceptrons, convolutional neural networks, recurrent neural networks, sequence-to-sequence models, generative adversarial networks, transformers, or a combination thereof.

In an embodiment, the training module 215-A may apply various preprocessing to the training videos 205 such as filtering, normalization, segmentation, or other transformations. The training module 215-A may furthermore include a feature extractor that extracts various features from the training videos 205 and generates respective feature vectors corresponding to each training video 205 that are inputted into a training algorithm. The features may represent various visual characteristics of the video and/or various latent features derived from the underlying videos 205. In other embodiments, the training module 215-A may operate directly on the training videos 205 without necessarily computing underlying features.

A machine learning model 220-A generated by the training module 215-A may comprise a set of model parameters representing weights or biases for applying to a set of input variables in accordance with one or more predefined functions. The learning process generally learns a set of model parameters from the training videos 205 that optimize an optimization criteria. In a supervised learning, the training module 215-A may iteratively apply a model 220 to a training video 205 to generate one or more outputs, compare the one or more outputs to the one or more labels to derive an error function, and apply an update algorithm (e.g., gradient descent or other technique) to update the model parameters in accordance with the optimization criteria (typically operating to reduce the error function). Over many iterations of the learning process utilizing a variety of training videos 105, the updates generally reduce error between the inferences and the labels, thus improving the predictive power of the model 220.

The inference module 225-A applies the one or more machine learning models 220-A to an input video 105 (that is unlabeled) to infer the timing and characteristics of the stapling events 114. Here, the inference module 225-A may apply similar preprocessing and/or feature extraction as used by the training module 215-A, if any. In an embodiment, the stapling events 114 may be represented as a vector of likelihood scores indicating respective inferred likelihoods of the various characteristics being present on a per-frame or per-segment basis. Likelihoods associated with the occurrence of a stapling event may be compared to a threshold to classify each frame or segment in a binary manner and identify the frames or segments that are positively detected as being associated with a stapling event. For each occurrence, the inferences associated with the highest likelihoods for each characteristic may furthermore be identified.

In some embodiments, the training module 215-A trains a single machine learning model 220, such as a multi-stage convolutional neural network, that jointly learns the occurrences of the stapling events and the various characteristics of the stapling events. The timing information and characteristics of each stapling event are then jointly inferred by the inference module 225-A. In other embodiments, the training module 215-A may separately train different machine learning models 220-A associated with different attributes of the stapling events. For example, a first machine learning model 220-A may be trained to detect the occurrences of the stapling events 114, a second machine learning model 220 may be trained to detect the color of a staple load, a third machine learning model may be trained to detect a manufacturer based on the stapler device used, etc. The inference module 225-A then similarly applies the set of models 220-A to generate respective inferences of the stapling events 114. In this embodiment, the various machine learning models 220-A may be trained (and applied) accordingly to different machine learning techniques that generate different types of machine learning models 220-A suitable each respective inference task.

While the training module 215-A and inference module 225-A are logically illustrated as separate components in FIG. 2, the algorithm employed by each module 215-A, 225-A may include overlapping functions (e.g., the same inference algorithm applied by the inference module 225-A may be employed by the training module 215-A during training). Thus, in practical implementation, the training module 215-A and inference module 225-A may be implemented at least in part using a shared set of executable instructions.

The training sequence store 255 comprises a database or other index that stores sequences of stapling events associated with medical procedures. The training sequences 255 may include stapling events 114 that are inferred by the inference module 225-A described above, or may include sequences obtained from external sources (e.g., manually entered data associated with historically performed medical procedures). In addition to storing timing and other characteristics associated with stapling event sequences, the training sequences may include various metadata relating to the underlying procedure. Such metadata may include, for example, the type of the surgical procedure, the surgeon performing the surgical procedure, the patient (or related demographic information thereof) on which the surgical procedure was performed, a date when the surgical procedure was performed, a patient recovery time following the surgical procedure, complications experienced by the patient following the procedure, or other descriptive information relating to the surgical procedure.

The training module 215-B trains one or more machine learning models 220-B for deriving various analytical data 118 associated with the training sequences 255. In one embodiment, the training module 215-B may employ a supervised learning approach that utilizes metadata as labels to generate a trained outcome model that infers relationships between the training sequences 255 and associated post-surgical outcomes. In another embodiment, the training module 215-B may employ an unsupervised or semi-supervised learning method to learn relationships between different training sequences 255. For example, the training module 215-B may train a clustering algorithm to cluster similar sequences and enable detection of outlier sequences that do not substantially conform to training sequences 255. Furthermore, the training module 215-B may learn relationships between individual stapling events within the sequence to enable inferences such as predicting characteristics of a future stapling event based on an observed partial sequence of stapling events. The training module 215-B may train a single machine learning model 220-B trained to jointly generate different types of inferences relating to an input stapling sequence 114 or may train multiple different machine learning models 220-B (which may be different types of machine learning models) to generate different types of inferences. The inference module 225-B applies the one or more machine learning models 220-B to a set of input stapling events 114 (that is unlabeled) to various analytical data 118 as described above. The training module 215-B and inference module 225-B may employ any of the same learning and inference techniques described above with respect to the training module 215-A and inference module 225-A.

The training modules 215, model stores 220, and inference module 225 are illustrated as being logically in FIG. 2 but in practice may be implemented utilizing at least some shared elements. For example, the model stores 220 may comprise a shared database and various functions employed by the training modules 215, 225 may be carried out using a shared set of computer instructions.

In some embodiments, the training modules 215 and inference modules 225 may be combined into respective joint modules 215, 225 that enable direct inference of one or more predictive analytical outputs 118 from an input video 105 without necessarily expressly detecting the sequence of stapling events 114. For example, a machine learning model 220 may be trained to directly infer a post-surgical outcome (e.g., recovery time, complications, etc.) based on an input video 105 without expressly inferring the sequence of stapling events 114 (although information relating to the stapling sequence may comprise a latent feature relevant to the model 220). In another example, a machine learning model 220 may directly output a similarity metric between a stapling sequence of an input video 105 and a baseline sequence without expressly generating and outputting the stapling events 114 themselves.

The machine learning approach described in FIG. 2 is intended to illustrate one example technique for generating analytical data 118, but other types of analytical data 118 may be generated without necessarily employing a machine learning approach. For example, various aggregations of stapling event data may be generated by applying one or more aggregation functions that do not rely on any machine learning model 220-B.

Figure 3:
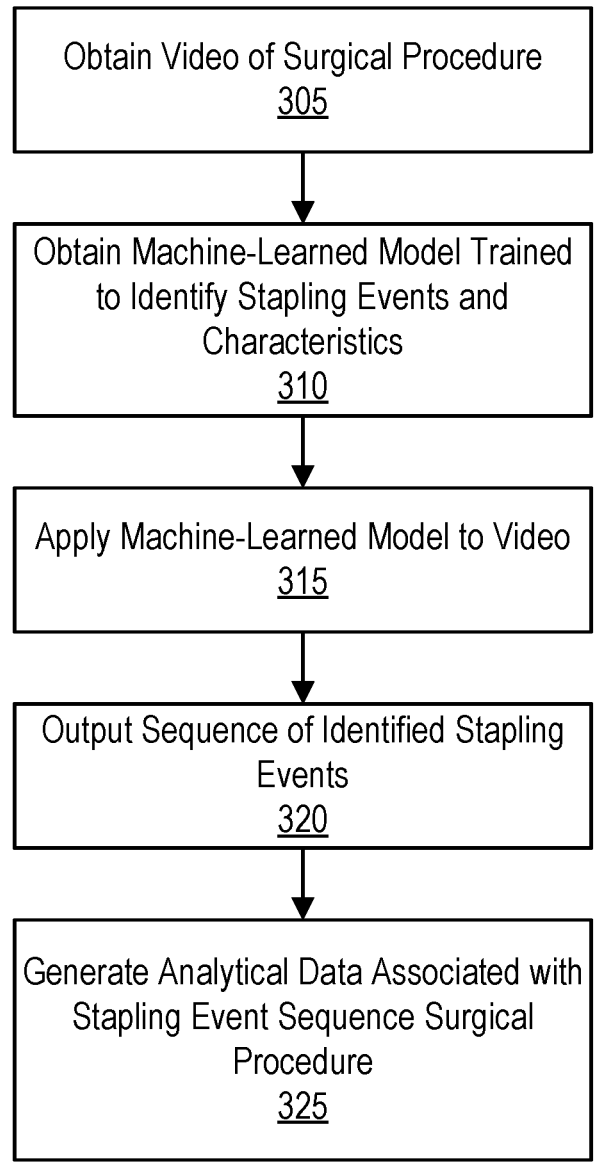
FIG. 3 is a flowchart of one embodiment of a method for detecting and characterizing stapling events from a video of a surgical procedure.

FIG. 3 is a flowchart of one embodiment of a method for detecting occurrences and characteristics of stapling events from an input video of a surgical procedure. In various embodiments, the method includes different or additional steps than those described in conjunction with FIG. 3. Further, in some embodiments, steps of the method may be performed in different orders than the order described in conjunction with FIG. 3.

An analysis system 110 obtains 305 a video of a surgical procedure and obtains 310 a machine learning model trained to detect stapling events from the video and to determine one or more characteristics of the stapling events. The analysis system 110 applies 315 the machine learning model to the video to detect one or more stapling events from the video and characteristics associated with each detected stapling events. As further described above in conjunction with FIGS. 1 and 2, the machine learning model may detect timing of the occurrences of the stapling event, as well as one or more characteristics of each stapling event (such as a length and/or color of staples used during the stapling event, an amount of time the patient's tissue was clamped together during the stapling event, and a firing rate of a stapler during the stapling event). The analysis system 110 outputs 320 the identified stapling events as a sequence of stapling events indicative of the detecting timing and characteristics. The analysis system 110 may furthermore generate 325 various analytical data (which may be based on another machine learning model) associated with the detected stapling event sequence such as predicted patient outcomes, similarities and/or differences relative to baseline sequences associated with the medical procedure, visualizations of various aggregate data, performance assessments relating to the medical procedure, recommendations associated with the medical procedure, etc.

Figure 4:
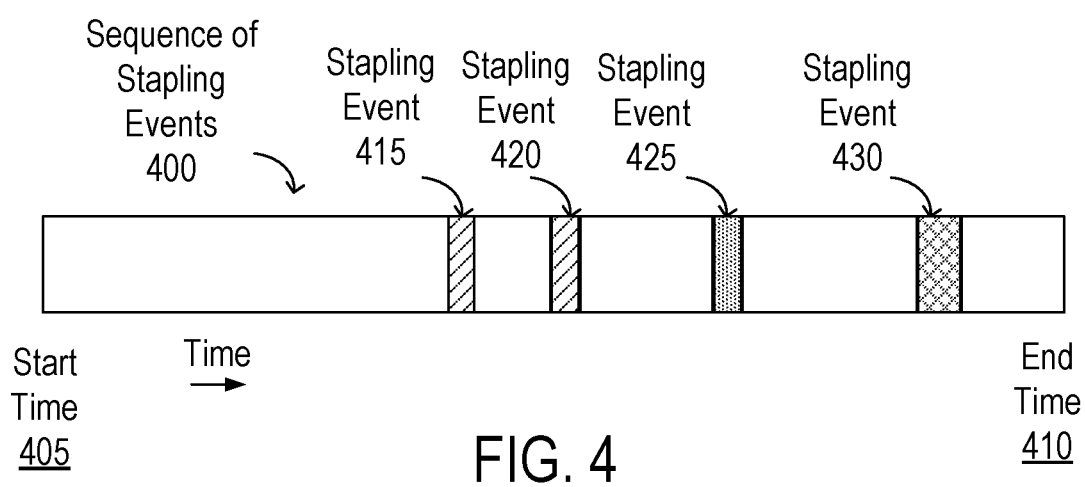
FIG. 4 is an example visualization of stapling events detected in a video of a surgical procedure.

FIG. 4 is example visualization of a sequence 400 of stapling events output from the analysis system 110 in relation to a video 105 of a surgical procedure. In the illustrated example, the detected sequence 400 is depicted on a timeline associated with the video 105 (having a start time 405 and an end time 410) Stapling events 415, 420, 425, 430 are detected at various times in the video 105 and their relative timing may be shown on the timeline. Furthermore, the relative lengths of each stapling event 415, 420, 425, 430 may be indicated. In an embodiment, each event 415, 420, 425, 430 may be color coded and/or labeled to indicate the type of staple loads used during the respective stapling event. In embodiment, the sequence 400 may be displayed together with the video 105 from which it was derived.

Embodiments of the described system 100 and corresponding processes may be implemented by one or more computing systems. The one or more computing systems include at least one processor and a non-transitory computer-readable storage medium storing instructions executable by the at least one processor for carrying out the processes and functions described herein. The computing system may include distributed network-based computing systems in which functions described herein are not necessarily executed on a single physical device. For example, some implementations may utilize cloud processing and storage technologies, virtual machines, or other technologies.

The foregoing description of the embodiments has been presented for the purpose of illustration; it is not intended to be exhaustive or to limit the embodiments to the precise forms disclosed. Persons skilled in the relevant art can appreciate that many modifications and variations are possible in light of the above disclosure.

Some portions of this description describe the embodiments in terms of algorithms and symbolic representations of operations on information. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible non-transitory computer readable storage medium or any type of media suitable for storing electronic instructions, and coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the inventive subject matter. It is therefore intended that the scope is not limited by this detailed description, but rather by any claims that issue on an application based hereon. Accordingly, the disclosure of the embodiments is intended to be illustrative, but not limiting, of the scope of the invention, which is set forth in the following claims.

What is claimed is:

1. A method for automatically characterizing stapling events in a surgical procedure based on an input video, the method comprising:
   receiving the input video of the surgical procedure;
   obtaining a first machine learning model trained by a supervised learning process using annotated training videos that are labeled to indicate timing of occurrences of stapling events and one or more characteristics of each of the stapling events;
   applying the first machine learning model to the input video to generate an inference that specifies a detected sequence of the stapling events according to their relative timing during the surgical procedure and one or more characteristics associated with each of the detected sequence of stapling events; and
   outputting the inference of the detected sequence of stapling events.

2. The method of claim 1, wherein the one or more characteristics comprises a length of a staple load used during a corresponding stapling event.

3. The method of claim 1, wherein the one or more characteristics comprises a color of a staple load and a manufacturer of a stapler delivering the staple load during a corresponding stapling event.

4. The method of claim 1, wherein the one or more characteristics comprises a clamping time associated with a corresponding stapling event, the clamping time indicative of an amount of time tissue of a patient is clamped together prior to a stapler load being delivered.

5. The method of claim 1, wherein the one or more characteristics comprises a detected presence or absence of a buttress in a stapler load delivered during a corresponding stapling event.

6. The method of claim 1, further comprising:
   obtaining a second machine learning model trained to infer one or more outcome attributes of surgical procedures based on respective sequences of stapler events occurring during the surgical procedures; and
   applying the second machine learning model to the detected sequence of stapling events inferred by the first machine learning model to predict one or more outcome attributes of the surgical procedure depicted in the input video.

7. The method of claim 6, wherein the one or more outcome attributes comprises a predicted recovery time for a patient.

8. The method of claim 6, wherein the one or more outcome attributes comprises one or more likelihoods of one or more post-surgical complications.

9. The method of claim 1, further comprising:
   comparing the detected sequence of surgical stapling events with a standard sequence of stapling events associated with the surgical procedure; and
   generating a similarity metric indicative of a similarity of the detected sequence with the standard sequence.

10. The method of claim 1, further comprising:
    aggregating the detected sequence of stapling events with a set of previously detected sequences of stapling events involving different surgeons performing the surgical procedure; and outputting one or more statistics based on an aggregation of the detected sequence of stapling events from the input video and the set of previously detected sequences of stapling events.

11. A non-transitory computer-readable storage medium storing instructions for automatically characterizing stapling events in a surgical procedure based on an input video, the instructions when executed by a processor causing the processor to perform steps comprising:

receiving the input video of the surgical procedure;

obtaining a first machine learning model trained by a supervised learning process using annotated training videos that are labeled to indicate timing of occurrences of stapling events and one or more characteristics of each of the stapling events;

applying the first machine learning model to the input video to generate an inference that specifies a detected sequence of the stapling events according to their relative timing during the surgical procedure and one or more characteristics associated with each of the detected sequence of stapling events; and outputting the inference of the detected sequence of stapling events.

12. The non-transitory computer readable storage medium of claim 11, wherein the one or more characteristics comprises a length of a staple load used during a corresponding stapling event.

13. The non-transitory computer readable storage medium of claim 11, wherein the one or more characteristics comprises a color of a staple load and a manufacturer of a stapler delivering the staple load during a corresponding stapling event.

14. The non-transitory computer readable storage medium of claim 11, wherein the one or more characteristics comprises a clamping time associated with a corresponding stapling event, the clamping time indicative of an amount of time tissue of a patient is clamped together prior to a stapler load being delivered.

15. The non-transitory computer readable storage medium of claim 11, wherein the one or more characteristics comprises a detected presence or absence of a buttress in a stapler load delivered during a corresponding stapling event.

16. The non-transitory computer readable storage medium of claim 11, further having instructions encoded thereon that, when executed by the processor, cause the processor to perform steps comprising:

obtaining a second machine learning model trained to infer one or more outcome attributes of surgical procedures based on respective sequences of stapler events occurring during the surgical procedures; and applying the second machine learning model to the detected sequence of stapling events inferred by the first machine learning model to predict one or more outcome attributes of the surgical procedure depicted in the input video.

17. The non-transitory computer readable storage medium of claim 16, wherein the one or more outcome attributes comprises a predicted recovery time for a patient.

18. The non-transitory computer readable storage medium of claim 16, wherein the one or more outcome attributes comprises a recovery time for a patient.

19. The non-transitory computer readable storage medium of claim 16, wherein the one or more outcome attributes comprises one or more likelihoods of one or more post-surgical complications.

20. A method for training a machine learning model to characterize stapling events in a surgical procedure based on a surgical video comprising:

obtaining a set of training videos depicting respective surgical procedures and respective labels identifying occurrences of stapling events and corresponding characteristics of the stapling events in the set of training videos;

applying a supervised machine learning algorithm to learn model parameters of the machine learning model such that the machine learning model, when applied to an input video, generates an inference that specifies a detected sequence of the stapling events according to their relative timing during the surgical procedure and one or more characteristics associated with each of the detected sequence of stapling events; and storing the machine learning model to a computer readable storage medium.

* * * * *